(12) United States Patent
Kouchi et al.

(10) Patent No.: US 7,914,449 B2
(45) Date of Patent: Mar. 29, 2011

(54) DIAGNOSTIC SUPPORT SYSTEM FOR DIABETES AND STORAGE MEDIUM

(75) Inventors: Yasuhiro Kouchi, Kagokawa (JP); Takeo Saitou, Kobe (JP); Hiromu Nakajima, Osaka (JP)

(73) Assignee: Sysmex Corporation (JP)

( * ) Notice: Subject to any disclaimer, the term of this patent is extended or adjusted under 35 U.S.C. 154(b) by 694 days.

(21) Appl. No.: 11/083,332

(22) Filed: Mar. 17, 2005

(65) Prior Publication Data

US 2005/0234311 A1   Oct. 20, 2005

(30) Foreign Application Priority Data

Mar. 17, 2004 (JP) ................. 2004-076397

(51) Int. Cl.
    *A61B 5/00*   (2006.01)
(52) U.S. Cl. ........................ 600/365; 600/300
(58) Field of Classification Search .............. 600/300, 600/365; 702/19; 703/11
    See application file for complete search history.

(56) References Cited

U.S. PATENT DOCUMENTS

| | | |
|---|---|---|
| 6,421,633 B1 | 7/2002 | Heinonen et al. |
| 2002/0120187 A1* | 8/2002 | Eiffert et al. ................. 600/407 |
| 2003/0058245 A1 | 3/2003 | Brazhnik et al. |
| 2004/0091424 A1 | 5/2004 | Asano et al. |
| 2005/0125158 A1* | 6/2005 | Schlessinger et al. .......... 702/19 |
| 2005/0131663 A1* | 6/2005 | Bangs et al. .................... 703/11 |

FOREIGN PATENT DOCUMENTS

| | | |
|---|---|---|
| CN | 1422136 A | 6/2003 |
| JP | 07-057018 A | 3/1995 |
| JP | 09-257790 A | 10/1997 |
| JP | 11-296598 | 10/1999 |
| WO | WO 01/72208 | 10/2001 |

OTHER PUBLICATIONS

Bergman, R. et al., "Quantitative Estimation of Insulin Sensitivity", *the American Physiological Society*, vol. 236, 1979, pp. 667-677.
Bergman, R. et al., "Physiologic Evaluation of Factors Controlling Glucose Tolerance in Man", *The American Society for Clinical Investigation, Inc.*, vol. 68, Dec. 1981, pp. 1456-1467.
Henan J Prev Med, 2001, vol. 12, No. 2.

* cited by examiner

*Primary Examiner* — Charles A Marmor, II
*Assistant Examiner* — Christian Jang
(74) *Attorney, Agent, or Firm* — Brinks Hofer Gilson & Lione

(57) ABSTRACT

A diagnostic support system for diabetes including an input device used for inputting diagnostic data including clinical testing data; a biological model having parameters and which represents a organ function related to diabetes as a numerical model; an predicting means for predicting parameter values suited for a patient based on the diagnostic data and the biological model; a pathological condition analyzing means for analyzing a diabetic pathological condition of a patient based on the parameter values predicted by the predicting means; a diagnostic support information generating means for generating diagnostic support information based on the analyzed pathological condition; and a diagnostic support information outputting means for outputting information obtained by the diagnostic support information generating means. A computer-readable storage medium is also disclosed.

17 Claims, 5 Drawing Sheets

DIAGNOSTIC SUPPORT SYSTEM FOR DIABETES AND STORAGE MEDIUM

This application claims priority under 35 U.S.C. §119 to Japanese Patent Application No. 2004-076397 filed Mar. 17, 2004, the entire content of which is hereby incorporated by reference.

FIELD OF THE INVENTION

The present invention relates to a diagnostic support system for diabetes and storage medium, and specifically relates to a diagnostic support system for analyzing the condition of diabetic patients and providing diagnostic support information which considers treatment methods and the like, and a storage medium for recording a computer program providing a computer with the functionality of the diagnostic support system for diabetes.

BACKGROUND

Diabetes is one of the most common lifestyle related disease. The pathologies of diabetes are classified as either type-1 diabetes or type-2 diabetes. Pathophysiologic conditions of type 2 diabetes are mainly classified into several subtypes from "hepatic glucose production", "insulin secretion capability", and "insulin resistance". The majority of diabetics are type 2 characterized by reduced insulin sensitivity, that is, an increase in insulin resistance and impaired insulin secretion from pancreatic β cells. In many cases, type 2 diabetes progresses without any subjective symptom, and a serious complication will develop if diabetes is left as it is.

Terribly, diabetes develops complications of peculiar angiopathy and neuropathy. Such complications occur when blood glucose control has not been satisfactory during progress of the disease for a long period, such as 5 years, 10 years or 20 years. For example, diabetic retinopathy and cataract, which are typical complications, cause vision disorder, and nephropathy causes proteinuria, swelling, and in course of time, leads to uremia. Neuropathy such as feeling of numbness in hands and legs and nerve pain may develop all over the body. Diabetes also accelerates arteriosclerosis, causing angina pectoris, myocardial infarction, cerebral apoplexy and cerebral thrombosis direct to the cause of death. Therefore, primary objects of treatment of diabetes are to prevent the complications and to inhibit the progress. In order to prevent complications, control of blood glucose is a very important factor.

For the treatment of type 2 diabetes, dietary therapy and exercise therapy are performed, which are intended to normalize blood glucose. However, when the above two treatments are not sufficient to normalize blood glucose, oral medicament or insulin injection is employed as medical treatment, so that blood glucose is desirably controlled.

Medicaments used for the treatment of diabetes are as follows:

(1) "sulfonylurea (SU) type drug" acting on pancreatic .beta. cells for promoting secretion of insulin;

(2) "biguanide (BG) type drug" acting mainly on the liver for elevating glucose disposal capacity in the liver and inhibiting release of glucose from the liver;

(3) ".alpha.-glucosidase inhibitors (AGI)" for depressing hyperglycemia after meals by inhibiting .alpha.-glucosidase (disaccharide hydrolysate enzyme) in the intestinal tract and holding up absorption of glucose through the intestinal tract;

(4) "insulin sensitizer (Thiazolidinedione, TZD)" for assisting a decrease of blood glucose by promoting the effects of insulin in the cells and reducing insulin resistance; and (5) Insulin.

The most suitable treatment program combining the dietary therapy, exercise therapy, and medication is prepared for controlling blood glucose depending on the state of the individual diabetic patients.

The determination of treatment programs is largely dependent on the knowledge and empirical rule of specialists. When analyzing the knowledge and experience of physicians who specialize in diabetes, it was found that treatment policy and programs are determined based on detailed management of the diseases of individual diabetic patients by physicians specializing in diabetes and their clinical findings, laboratory test results and the like.

For example, based on such clinical findings and laboratory results, when the pathophysiologic condition of a diabetic patient is classified from four factors of "excessive hepatic glucose production", "insulin secretion capability", "insulin resistance", and "glucose toxicity" which qualifies these factors, the pathophysiologic condition of diabetes is classified as follows.

A. Type 1 Diabetes

B. Type 2 Diabetes (Peripheral Insulin Resistance); Utilization of glucose in muscles or peripheries is lowered. Most of the patients are obese.

C. Type 2 Diabetes (Excessive Hepatic Glucose Production); The promotion effect of hepatic glycogen synthesis and inhibitory action of gluconeogenesis are lowered. Even though patients are not obese, visceral fat is accumulated in many cases.

D. Type 2 Diabetes (Impaired Insulin Secretion); Secretion of insulin is incomplete because of exhausted pancreatic .beta. cells. Patients are not obese, but are rather emaciated.

It is difficult to have adequate control of blood glucose levels in the standard treatment programs for these conditions, and an optimum treatment program must combine diet, exercise, and medications which correspond to the individual condition. General practitioners and general internists who are not specialists in diabetes may not necessarily be able to realize an optimum treatment program for an individual patient, nor achieve a desired blood glucose level. However, even a general practitioner or general internist may provide treatment suited for an individual diabetic patient if the non-specialist general practitioner or general internist is provided with diagnostic support information to accurately and quantitatively manage the diabetic condition.

Although a number of diagnostic support systems for diabetes exist, most such systems simply monitor the measurements of the patient's blood glucose level, and simply determine an insulin dose from the measurements such as the patient's blood glucose level, and do not provide adequate support information for the non-specialist (for example, refer to Japanese Laid-Open Patent Publication Nos. 10-332704 and No. 11-296598). Furthermore, Diagnostic Criteria for diabetes of the Japan Diabetes Society are well known. Patients are classified as either normal type, borderline diabetic type, or diabetic type based on the presence/absence of a typical diabetic condition and the results of an oral glucose tolerance test, and patients who are classified as diabetic type based on two tests are diagnosed as diabetic.

Existing computer systems which perform diabetes diagnostic support often provide automated determinations based on this diagnostic standard. For example, such systems will input the results of the oral glucose tolerance test and the like, and automatically compare the input data with predetermined standard values, classify the patient as either normal type, borderline diabetic type, or diabetic type, and output the result.

High precision systems also exist which determine whether or not a patient is obese by inputting the patient's combined height and weight, and adding functions to automatically select the medication to be administered.

Since these conventional systems cannot perform detailed analysis of the condition of an individual patient, however, physicians using these conventional systems are not able to provide detailed management of the patient's condition. Accordingly, the patient's condition cannot be properly managed without the subjectivity and broad experience of a specialist, and physicians who are not diabetes specialists and physicians of lesser experience in diagnosing diabetes are unable to make accurate determinations. Even the determinations of specialists are dependent on subjective factors and varying degrees of experience, such that some divergence is inevitable.

BRIEF SUMMARY

The scope of the present invention is defined solely by the appended claims, and is not affected to any degree by the statements within this summary.

In consideration of the above information, an object of the present invention is to provide a diagnostic support system capable of estimating the cause of disease from input testing values, and providing support information which aids management of the patient's condition and diagnosis by non-diabetes specialist physicians.

The first aspect of the present invention relates to a diagnostic support system for diabetes comprising an input device used for inputting diagnostic data including clinical testing data; a biological model having parameters and which represents a organ function related to diabetes as a numerical model; an predicting means for predicting parameter values suited for a patient based on the diagnostic data and the biological model; a pathological condition analyzing means for analyzing a diabetic pathological condition of a patient based on the parameter values predicted by the predicting means; a diagnostic support information generating means for generating diagnostic support information based on the analyzed pathological condition; and a diagnostic support information outputting means for outputting information obtained by the diagnostic support information generating means.

The second aspect of the present invention relates to a diagnostic support system for diabetes comprising an input device used for inputting diagnostic data including clinical testing data; a biological model having parameters and which represents a organ function related to diabetes as a numerical model; an predicting means for predicting parameter values suited for a patient based on the diagnostic data and the biological model; and a treatment simulating means for inputting the parameter values predicted by the predicting means to the biological model, and simulating the effects of the treatment by simulated execution of the treatment based on a hypothetical treatment policy.

The third aspect of the present invention relates to a computer-readable storage medium for recording a computer program which enables a computer provided with an input device and an output device to function as a diagnostic support system for diabetes, wherein the computer program comprises a step of receiving the input of diagnostic data which includes clinical testing data to the computer through the input device; a step of, in the computer, predicting parameter values which are suited for a patient based on diagnostic data and a biological model having parameters and which represents a organ function related to diabetes as a numerical model; a step of, in the computer, analyzing a diabetic pathological condition of a patient based on the predicted parameter values; a step of, in the computer, generating diagnostic support information based on the analyzed pathological condition; and a step of, in the computer, outputting the generated diagnostic support information through the output device.

DETAILED DESCRIPTION OF THE DRAWINGS AND THE PRESENTLY PREFERRED EMBODIMENTS

The embodiment of the present invention is described hereinafter with reference to the drawings.

Figure 1:
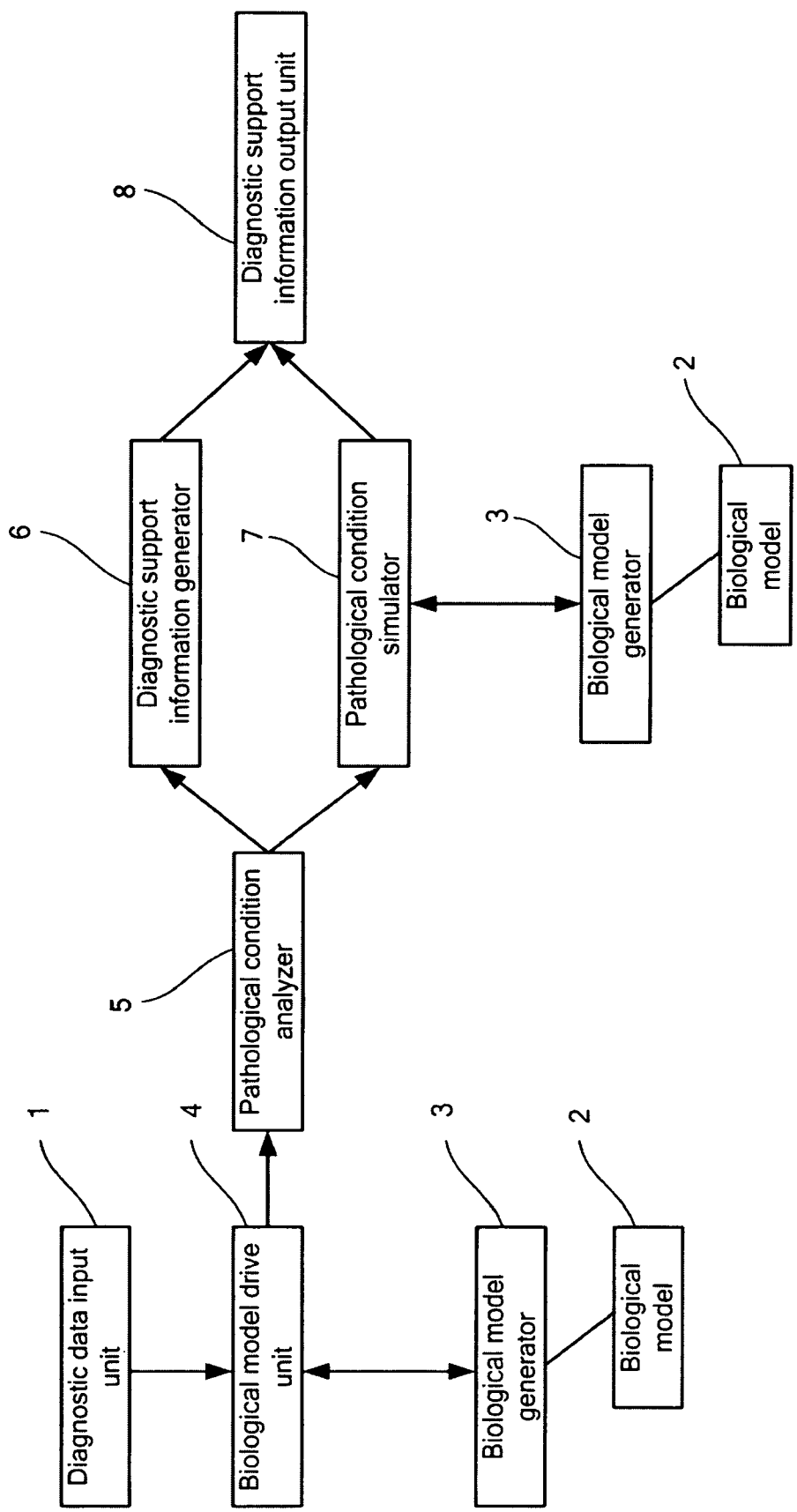
FIG. 1 is a function block diagram briefly showing the structure of an embodiment of the diagnostic support system for diabetes of the present invention.

FIG. 1 is a function block diagram briefly showing the structure of the embodiment of the diagnostic support system for diabetes of the present invention. As shown in FIG. 1, a diagnostic support system 10 of the present embodiment has various function blocks including a diagnostic data input unit 1, biological model 2, biological model drive unit 4, biological model generator 3, pathological condition analyzer 5, diagnostic support information generator 6, pathological condition simulator 7, and diagnostic support information output unit 8. The respective function blocks are realized by cooperative operation of the following hardware structures and computer programs.

Figure 2:
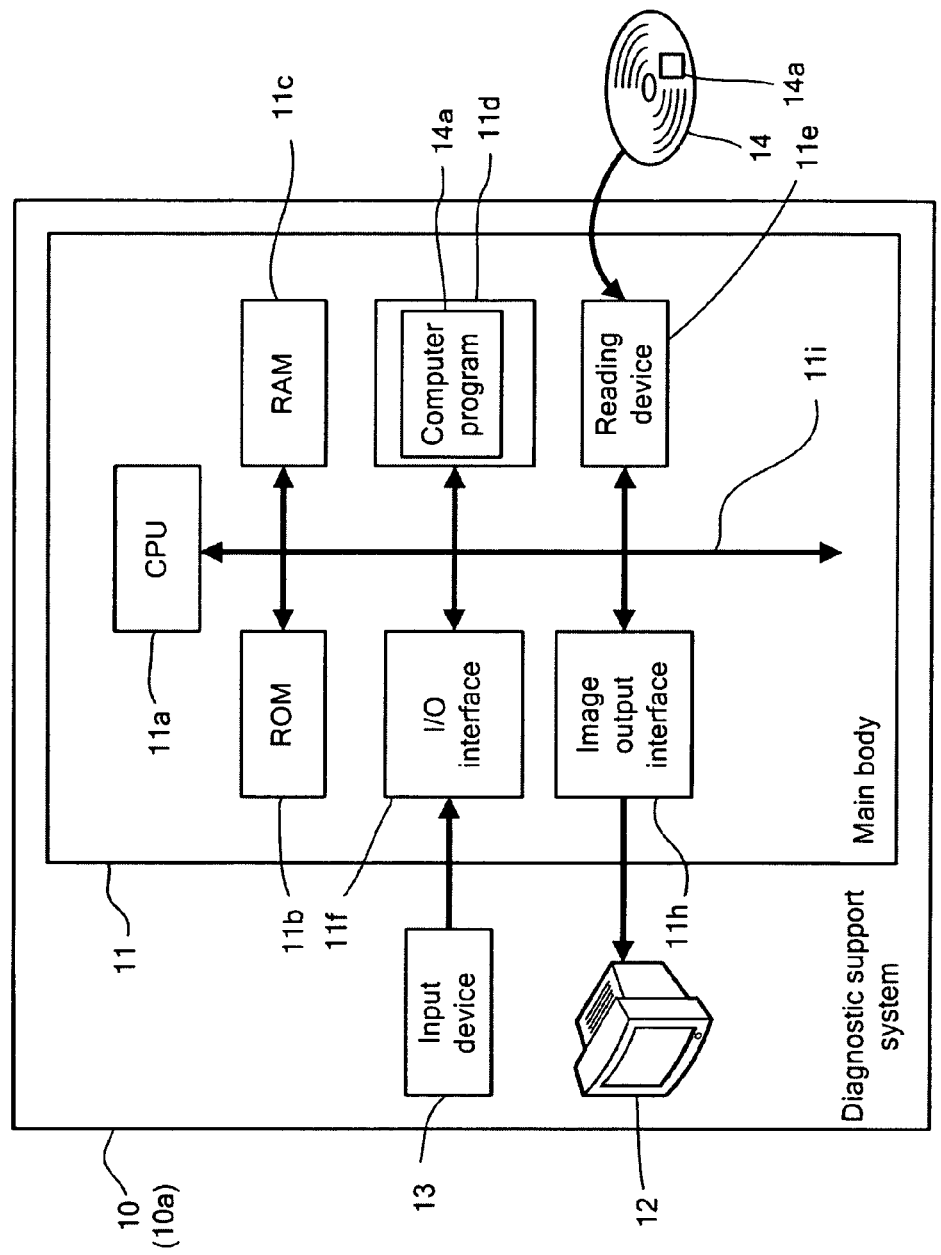
FIG. 2 is a block diagram showing the hardware structure of the embodiment of the diagnostic support system for diabetes of FIG. 1.

FIG. 2 is a block diagram showing the hardware structure of the embodiment of the diagnostic support system for diabetes of the present invention. The diagnostic support system 10 of the present embodiment of the invention is a computer 10a which mainly includes a body 11, display 12 and input device 13. The body 11 mainly includes a CPU 11a, ROM 11b, RAM 11c, hard disk 11d, reading device 11e, input/output (I/O) interface 11f, communication interface 11g, and image output interface 11h; the CPU 11a, ROM 11b, RAM 11c, hard disk 11d, reading device 11e, I/O interface 11f, and image output interface 11h are connected by a bus 11i to enable data communications.

The CPU 11a is capable of executing computer programs recorded in ROM 11b, and computer programs loaded in the RAM 11c. Each of the previously mentioned function blocks can be realized and the computer 10a can function as the diagnostic support system 10 when the CPU 11a executes an application program 14a described later.

The ROM 11b may be formed by a mask ROM, PROM, EPROM, EEPROM and the like, and is used to store the computer programs excited by the CPU 11a and data and the like used by these programs.

The RAM 11c is formed by an SRAM, DRAM and the like. The RAM 11c is used to read the computer programs stored in the ROM 11b and hard disk 11d. Furthermore, the RAM 11c is used as a work area by the CPU 11a when these computer programs are being executed.

The hard disk 11d contains various types of installed computer programs executed by the CPU 11a, such as an operating system and application programs and the like, as well as the data used when executing these computer programs. The data used when executing the application program 14a described later is also installed on the hard disk 11d.

The reading device 11e is formed by a flexible disk drive, CD-ROM drive, DVD-ROM drive or the like, and is capable of reading computer programs and data recorded on a transportable storage medium 14. Furthermore, the transportable storage medium 14 stores the application program 14a which enables a computer to function as the diagnostic support system for diabetes of the present invention. The computer 10a is capable of reading the application program 14a of the present invention from the transportable storage medium 14, and installing the application program 14a on the hard disk 11d.

The application program 14a is not only provided on the transportable storage medium 14, inasmuch as it may also be provided by transmission over an electrical communication line from an external device connected to the computer 10a so as to allow communication through an electrical communication line (whether wired or wireless). For example, the application program 14a may be stored on the hard disk of a server computer on the internet, such that the computer 10a can access the server computer and download the computer program and install the computer program on the hard disk 11d.

Also installed on the hard disk 11d is an operating system which provides a graphical user interface environment, such as, for example, Windows (registered trademark), a commercial product of Microsoft Corporation, USA. In the following description, the application program 14a of the present embodiment performs the operations of an operating system.

The I/O interface 11f includes a serial interface, such as, for example, USB, IEEE1394, RS-232C or the like, parallel interface, such as, for example, SCSI, IDE, IEEE1284 or the like, and analog interface such as, for example, a digital-to-analog (D/A) converter, analog-to-digital (A/D) converter or the like. An input device 13, which includes a keyboard and mouse, is connected to the I/O interface 11f, and a user can input data to the computer 10a by using the input device 13.

The image output interface 11h is connected to the display 12 formed by an LCD, CRT or the like, and image signals corresponding to the image data from the CPU 11a are output to the display 12. The display 12 displays images (screens) in accordance with the input image signals.

The diagnostic data input unit 1 shown in FIG. 1 is used to input the values of clinical testings of blood glucose level and so on, information on findings obtained from doctor's question, and other information into the system; and this input unit 1 is formed by the input device 13 shown in FIG. 2, I/O interface 11f, and computer programs related to receiving information input from the input device 13. Although the diagnostic data input unit 1 is formed by the input device 13 in the present embodiment, the present invention is not limited to this mode inasmuch as various input device other than the input device 13 may be provided, for example, optical character recognition (OCR), scanner and the like; furthermore, when various types of information are recorded beforehand in a database or the like accessible to the computer 10a, the information may be input by the computer 10a accessing the database. The input information is stored on the hard disk 11d so as to be usable by the biological model generator 4 and the like.

In the present embodiment, input diagnostic data includes, at least, an oral glucose tolerance test insulin value (μu/ml), blood glucose level (mg/dl), insulin values a after fasting and 2 hr after eating (μu/ml), blood glucose level b (mg/dl), HOMA-IR value (=a times b/405), quantitative 24 hours urine C-peptide (μg), glycated hemoglobin index $HbA_{1c}$, presence/absence of weight loss, BMI value, ΔIRI/ΔBS, whether or not the patient is urine ketone body-positive and the like. However, the information is not limited to that listed above, and other testing values and the like may be input as necessary. Examples of other such information include the state of obesity, the state of fasting and postprandial blood glucose level, the state of dietary intake of carbohydrate and the like.

The biological model 2 is a model which represents the organ functions related to diabetes as a numerical model, for example, insulin secretion function in the pancreas, glucose uptake and production function in the liver, and glucose metabolism function using insulin in peripheral tissue can be represented. An example of a method capable of representing the model is a differential equation in which substance concentrations are variables. However, the present invention is not limited to the above examples inasmuch as other methods may be used to represent the model, including other organ functions, and other functions as necessary. The biological model 2 has structural components common to each patient, and parameters, that is, variables, which differ for each patient.

Examples of the biological model 2 are described by Bergman, who uses a model which mathematically represents a minimal model, as disclosed in Bergman et al., *American Journal of Physiology*, vol. 236(6), p. E-667-77 (1979), and Bergman et al., *Journal of Clinical Investigation*, vol. 68(8), p. 1456-67 (1981).

This minimal model mathematically represents plasma glucose concentration, plasma insulin concentration, and amount of acting insulin at the insulin action site of peripheral tissue, that is, remote insulin, as variables. In this case, when the plasma glucose concentration at time t is designated G(t), plasma insulin concentration is designated 1(t), and remote insulin is designated X(t), then G(t), I(t), and X(t) the respective time differentials can be described on the left side of the differential equations below.

$$\frac{dG(t)}{dt} = -pI(G(t) - Gb) - X(t)G(t)$$

$$\frac{dX(t)}{dt} = -p2\,X(t) + p3(I(t) - Ib)$$

$$\frac{dI(t)}{dt} = -n(I(t) - Ib) + \gamma(G(t) - h) \text{ when } G(t) > h \text{ and}$$

$$= -n(I(t) - Ib) + \gamma(G(t) - h) \text{ when } G(t) \leq h$$

Where the parameters in the equations are defined as follows, and each parameter can represent different values for each patient.

p1: Non-insulin-dependent glucose metabolism rate
Gb: Basal glucose concentration
p2: Insulin uptake at insulin action site
p3: Insulin consumption rate relative to insulin-dependent glucose metabolism
Ib: Basal insulin concentration
n: Insulin consumption per unit time γ: Insulin secretion sensitivity relative to glucose simulation h: Blood glucose threshold value at which insulin secretion begins The biological model drive unit 3 performs calculations for reproducing the behavior of a living body using the biological model 2. The behavior of a living body also may be calculated using, for example, MatLab (The MathWorks, Inc.), and E-Cell (public domain software of Keio University). Other calculation systems may also be used.

When the minimal model is used as the biological model 2, numerical calculation software capable of calculating differential equations by optional parameters and optional time intervals may be used as the biological model drive unit 3.

The biological model generator 4 predicts the parameter values of the biological model 2 so as to produce agreement between the output of the biological model drive unit 3 and the input diagnostic data. Well-known method of least squares, method of steepest descent, and method of genetic algorithms may be used as the parameter values prediction method. The present invention is not limited to these methods, and other methods also may be used as necessary.

When the minimal model is used as the biological model 2, the first step is to estimate p1, p2, p3, and Gb values among the aforesaid parameters using the well-known method of least squares, method of steepest descent, and method of genetic algorithms so as to minimize errors in the G(t) output by the biological model drive unit 3, using the plasma insulin concentration change data of intravenous glucose tolerance test as the diagnostic data. The next step is to estimate the values γ, n, h, and Ib among the aforesaid parameters using the same well-known methods so as to minimize errors in the I(t) output by the biological model drive unit 3 using the plasma glucose concentration change data from the intravenous glucose tolerance test as the diagnostic data.

The pathological condition analyzer 5 analyzes the disease condition by associating the parameter values generated by the biological model generator 4 with the three types of diabetic conditions, that is, excessive hepatic glucose production, insulin secretion capability, and insulin resistance, comparing the data to parameter values of healthy persons determined beforehand, and analyzing the pathological condition by detecting differences in the parameters. For example, among the minimal model parameters, γ can be associated with insulin secretion capability, Gb can be associated with excessive hepatic glucose production, and p3 can be associated with insulin resistance. Furthermore, in regard to specific parameters, upper and lower limit values of healthy persons may be set, so as to determine as abnormal any values outside this range. Moreover, normal and abnormal values may be determined by the ratio of typical values of healthy persons and the generated patient parameter values.

The diagnostic support information generator 6 generates support information starting with the optimum considered treatment method based on treatment determination standards described later, using the pathological condition patterns output by the pathological condition analyzer 5, and a database storing specialist medical software and diagnostic data input from the diagnostic data input unit 1.

The database, which stores the specialized knowledge of specialist physicians, includes specialist knowledge related to medications for treating diabetes, knowledge related to exercise programs, and knowledge related to diet programs, and systematically organizes such knowledge as treatment policies in accordance with the pathological condition patterns, clinical findings of patients, surgical case histories and the like. This information is stored in memory devices, such as the hard disk 11d and RAM 11c and the like.

Knowledge of medications includes candidate drugs which can be administered for each pathological condition, drug selection ranking and dosage corresponding to the clinical findings, and types (contraindication information) of drugs which cannot be administered in a patient in a particular condition. The drug dosage rate is included as a function of the intensity of the parameter such as whether or not there is organic disorder of the kidneys, for example, and the influence of disease etiology on diabetes in each patient.

For example, policies for drug administration combining AGI and TZD provide the maximum effect of improved insulin resistance among the etiology of diabetes for a particular patient, and of course consider conditions such as the absence of cardiac insufficiency, absence of electrolyte anomalies, and absence of past surgery of the gastrointestinal track.

Knowledge of exercise programs includes exercise intensity, amount of exercise, and recommended type of exercise corresponding to each disease condition.

Knowledge of dietary programs includes allowed calorie intake, and allowed intake of each nutrient corresponding to each disease condition.

The pathological condition simulator 7 uses the biological model characteristic of a patient generated by the biological model generator 4 to predict the disease condition after treatment of the patient. For example, regarding a patient for whom the maximal influencing etiology is impaired secretion of insulin before treatment, when the simulation result hypothesizes administration of insulin and observations include elevated insulin secretion and decreasing glucose production, but a rise in utilization of glucose is not observed, the maximal influencing etiology is insulin resistance after treatment, and a result signifying this outcome is output.

The diagnostic support information output unit 8 outputs support information, such as treatment methods generated by the diagnostic support information generator 6, condition or treatment result predicted by the pathological condition simulator 7 and the like.

As shown in FIG. 2, the diagnostic support information output unit 8 is formed by the display 12, image output interface 11h, and computer program relating to the output of information to the display 12. In the present embodiment, the diagnostic support information output unit 8 is formed by the display 12, however, the present invention is not limited to this mode inasmuch as, other than the display 12, a device such as, for example, a printer or the like may also be provided.

Figure 3:
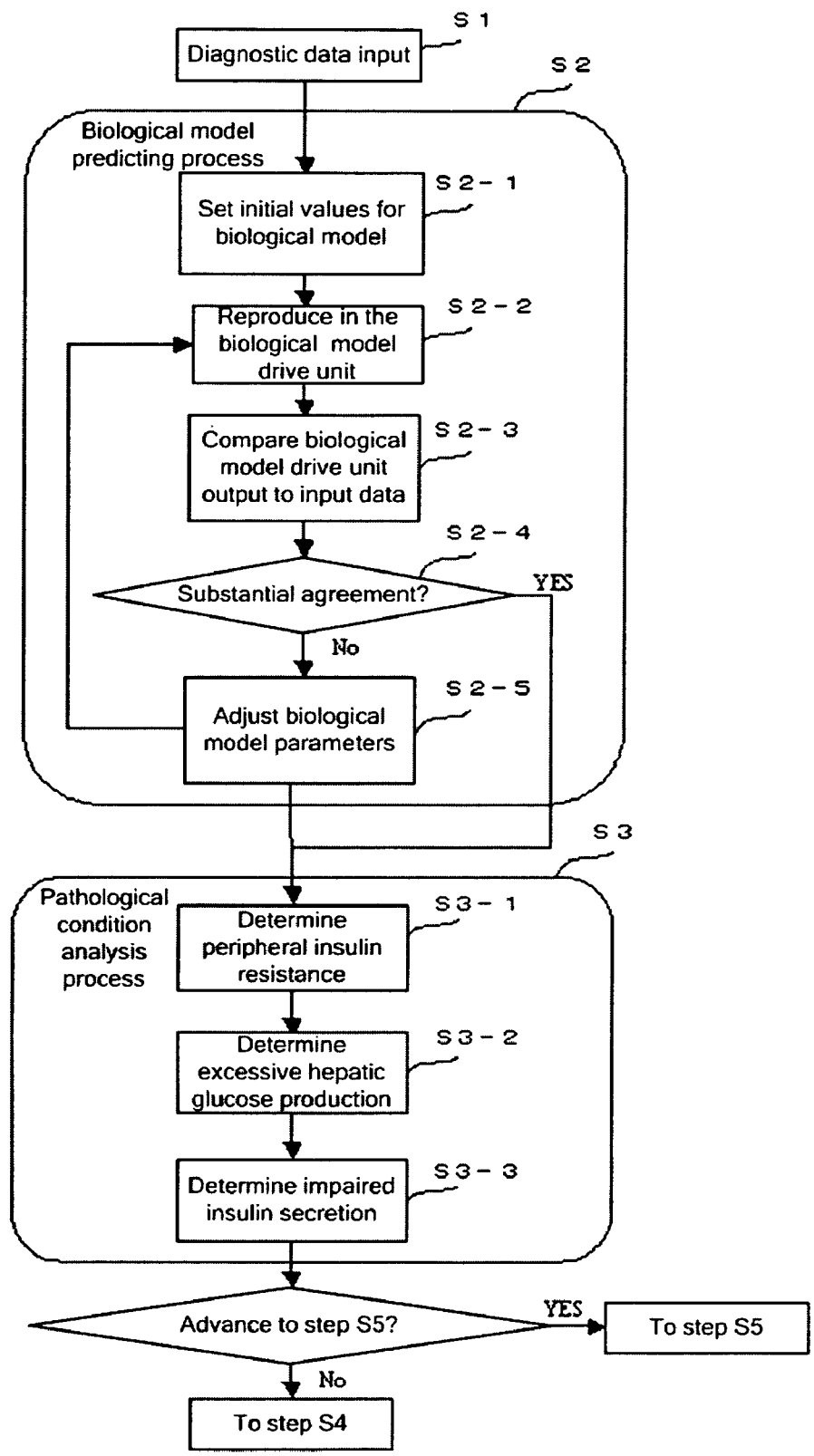
FIG. 3 is a flow chart showing all the processing of the embodiment of the diagnostic support system for diabetes of the present invention.
Figure 4:
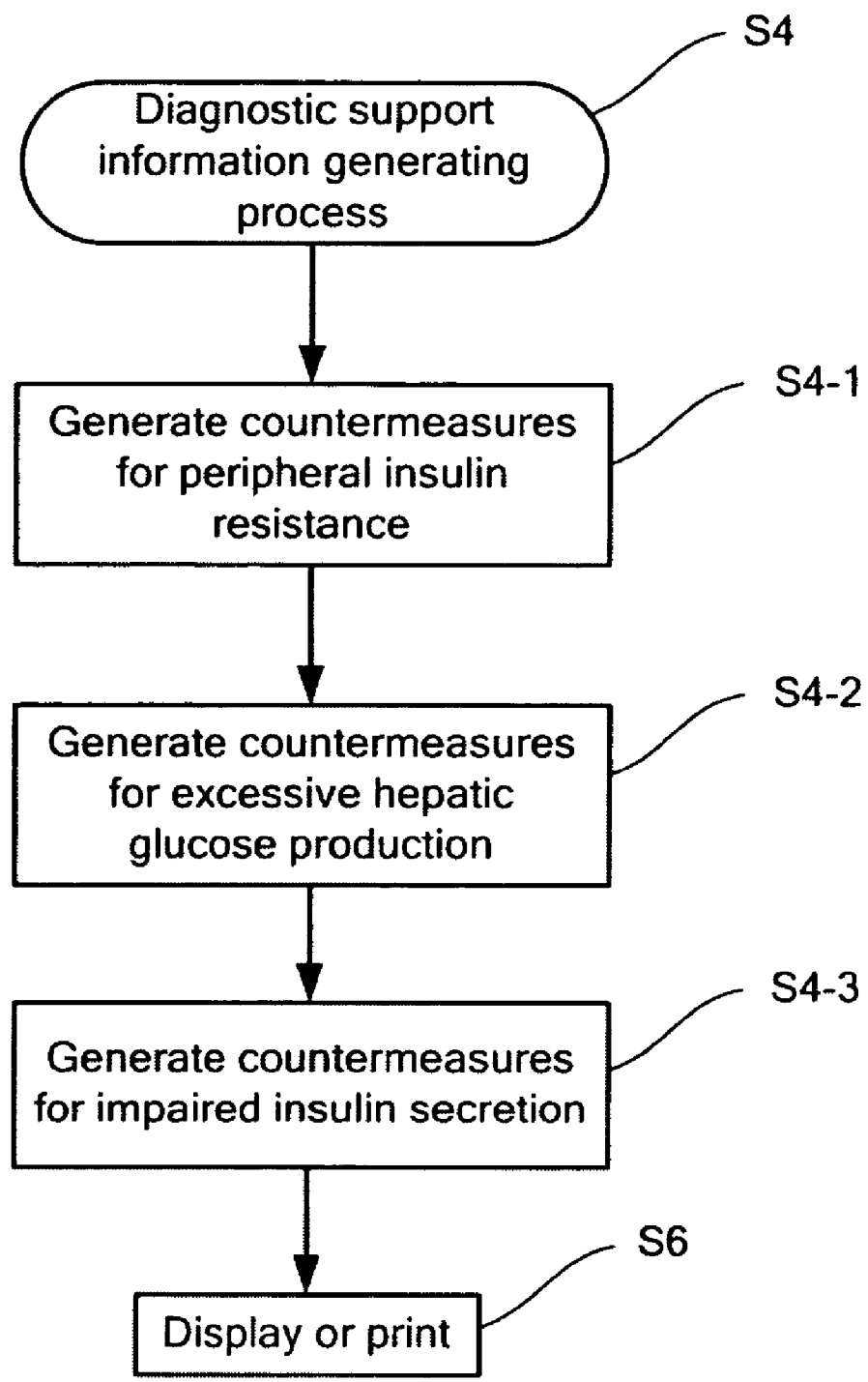
FIG. 4 is a flow chart showing the diagnostic support information generating process of the embodiment of the diagnostic support system for diabetes of the present invention.
Figure 5:
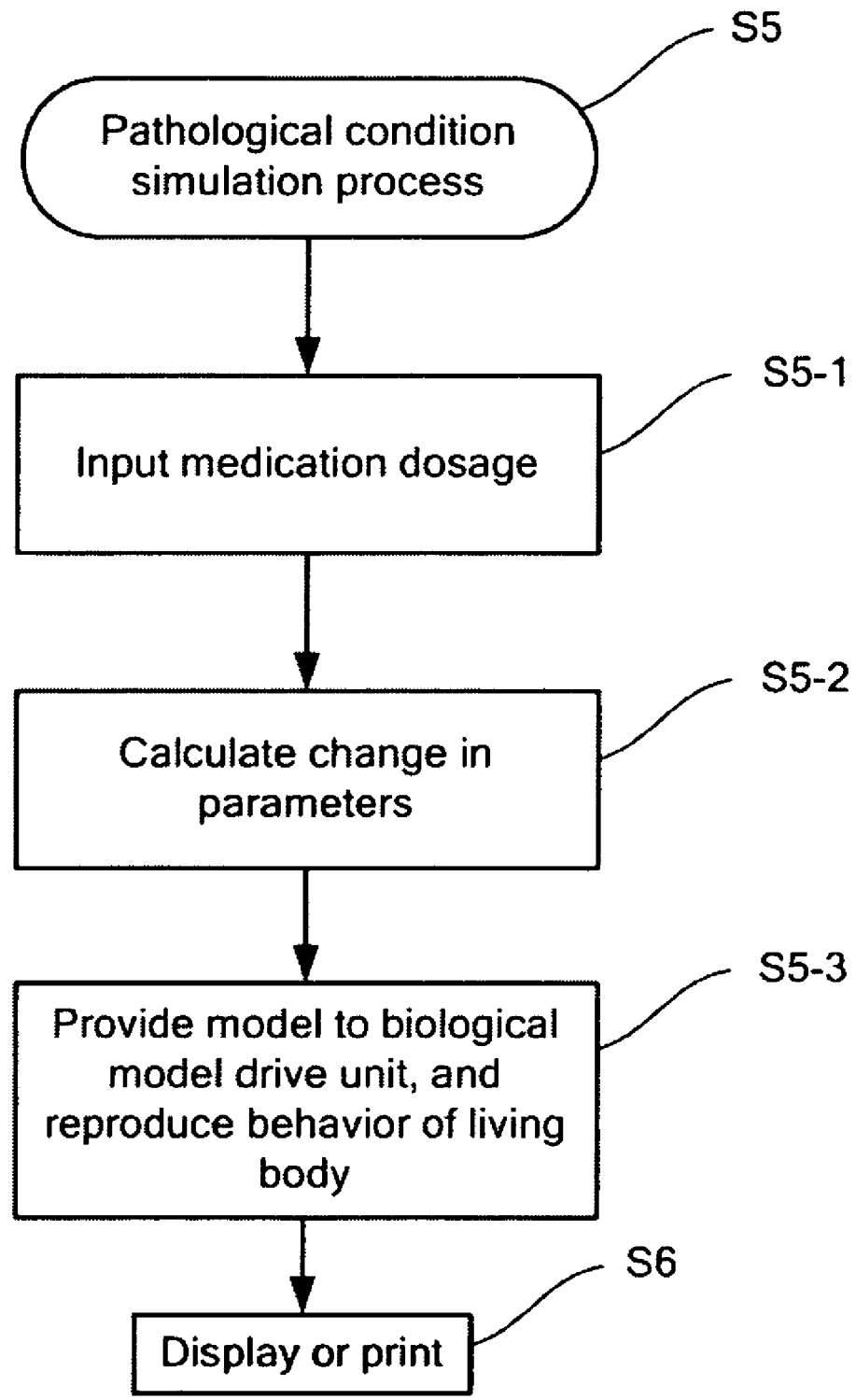
FIG. 5 is a flow chart showing the disease condition simulation process of the embodiment of the diagnostic support system for diabetes of the present invention.

The contents of processes performed by the diagnostic support system of the present invention are described below. FIGS. 3, 4, and 5 are flow charts showing the flow of the processing performed by the diagnostic support system of the present invention. First, in step S1, the CPU 11a receives from the input device 13 the input of diagnostic data for a patient as previously described.

Then, the CPU 11a starts the biological model predicting process (step S2). In this step, the CPU 11a sets predetermined initial values as the parameter values of the biological model 2 (step S2-1), and reproduces the behavior of a living body in the biological model drive unit 3 (step S2-2).

Then, the CPU 11a compares the output of the biological model drive unit 3 with the input diagnostic data, and determines whether or not both are in substantial agreement (steps S2-3, S2-4). When the data are not in substantial agreement, the CPU 11a updates the parameter values, and returns to step S2-2 and repeats the process.

When the output of the biological model generator 3 and the input diagnostic data are in substantial agreement, the CPU 11a outputs the parameter values at this time, and the process continues to the disease condition analysis step of S3.

Next, the CPU 11a starts the disease condition analysis process (step S3). The disease condition analysis process mainly performed the following three determination processes.

Step S3-1: Determine peripheral insulin resistance
Step S3-2: Determine excessive hepatic glucose production
Step S3-3: Determine impaired insulin secretion For example, when p3 in the minimal model is parameters expressing the amount of glucose metabolized per unit time relative to the insulin concentration in peripheral tissue, then a patient for whom this parameter is reduced can be determined to have peripheral insulin resistance.

When Gb in the minimal model is parameters expressing a blood glucose value as a base value at which glucose production is suppressed, then a patient for whom this parameter is increased can be determined to have excessive production in the liver.

When γ in the minimal model is parameters expressing the amount of insulin produced per unit time by the pancreas relative to glucose stimulation, then a patient for whom this parameter is reduced can be determined to have impaired insulin secretion capability.

When each step of the determination process is executed, then in each step the CPU 11a calculates a score, and the scores are temporarily stored in the RAM 11c or hard disk 11d. For example, in step S3-1, the CPU 11a executed the peripheral insulin resistance determination process top determine an evaluation value (designated score A) which represents the degree of influence insulin resistance has in the etiology of diabetes. The method of calculating the score A may be, for example, to divide p3 in the minimal model, that is, the insulin consumption rate relative to the insulin-dependent glucose metabolism, by the normal subject standard value. The score A is temporarily stored, and used in the subsequent diagnostic support information generating process (step S4).

Similarly, in step S3-2, the CPU 11a calculates a score B, which is the evaluation value of excessive glucose production, and in step S3-3, the CPU 11a calculates a score C for impaired insulin secretion. The method of calculating the score B may be, for example, to divide Gb in the minimal model, that is, the glucose concentration base value, by the normal subject standard value. The method of calculating the score C may be, for example, to divide h in the minimal model, that is, the blood glucose threshold value at which insulin secretion starts, by the normal subject standard value. The larger these numerical scores are, the greater the influence on disease etiology.

The CPU 11a advances to the support information generating process (step S4), and determines whether to continue to the pathological condition simulation (step S5). This determination may initiate a display prompting for user input so as to specify the process to be executed by specific key input determined by the user. Alternatively, when there is input in step S1, information specifying which processes may be input by a user beforehand. Furthermore, when this multipoint determination is not necessary, the step S5 may be sequentially executed after the CPU 11a has executed step S4.

In the diagnostic support information generating process of step S4, the CPU 11a may execute processes among the four processes described below according to the magnitude relationship of the three scores (A, B, C) determined in step S2.

Step S4-1: Executed when the peripheral insulin resistance is determined to be maximum.
Step S4-2: Executed when excessive hepatic glucose production is determined to be maximum.
Step S4-3: Executed when insulin secretion reduction is determined to be maximum.

Among these three processes, the CPU 11a generates support information, which includes treatment policies, medications to be administered and the like, for the respective pathological conditions based on a predetermined treatment determination standard.

For example, when peripheral insulin resistance is determined to be greatest, information specifying the resistance enhancing drug TZD as the most suitable can be generated by the CPU 11a.

When excessive hepatic glucose production is determined to be greatest, information specifying the glucose production suppressing drug BG as most suitable can be generated by the CPU 11a.

Similarly, when insulin secretion reduction is determined to be greatest, information specifying the insulin secretion stimulating drug SU as most suitable can be generated by the CPU 11a.

After step S4, the CPU 11a displays the generated diagnostic support information on the display 12, or send the data to the printer (step S6).

In the pathological condition simulation process (step S5), the CPU 11a uses the determined parameter values to predict the condition of the patient after treatment. The condition prediction is accomplished, for example, by the CPU 11a calculating each function value representing the parameter values by inputting information on specific dosages of certain medications, and increasing or decreasing each parameter value to have these parameter values affect the biological model drive unit. Thereafter, the CPU 11a advances to the process of step S6, and the information serving the diagnostic supports determined in steps S2, S3, and S5 is displayed on the display 12, or sent to a printer. The processes described above are the overall flow of the diagnostic support system of the present invention.

After the policies analyzing the pathological condition have been determined, then in step S6, diagnostic support information including these determined policies is provided to the physician. Since identical testing and analysis are performed at re-testing and subsequent testing of an individual patient and diagnostic support information is provided together with numerical analysis results (scores), it is possible to objectively and precisely manage the change in the patient's condition over the time course, and implement treatment based on suitable determination according to the patient's condition over time.

For example, the physician is not only made aware of changes in condition according to simple classifications by viewing the change in scores, the physician can also confirm whether or not the degree of the condition has changed from the quantified scores, thereby making more appropriate determinations and treatment possible. Furthermore, since analysis of a pathological condition and treatment policies can be obtained by uniform treatment determination standards prepared beforehand without reliance on subjective judgment and experience which is rife with indefinite factors, it is possible to arrive at determinations and treatments identical to or very similar to those of specialist physicians without the physician being a specialist in diabetes.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A diagnostic support system for diabetes comprising:
an input device for inputting diagnostic data to a predicting device including clinical testing data of a patient,
wherein the predicting device predicts parameter values suited for the patient based on the diagnostic data and a biological model, the biological model having parameters and which represent an organ function related to diabetes as a numerical model,
wherein the biological model includes pancreas, liver, and peripheral tissue models, and the pancreas model represents insulin secretion, the liver model represents glucose uptake and production, and the peripheral tissue model represents glucose metabolism through insulin, and
wherein the biological model comprises parameters which respectively represent non-insulin-dependent glucose metabolism rate, basal glucose level, insulin uptake function at the insulin action site, insulin consumption rate relative to an insulin dependent glucose metabolism, basal insulin concentration, amount of insulin consumed per unit time, insulin secretion sensitivity relative to glucose stimulation, and blood glucose level threshold at which insulin secretion begins;
a pathological condition analyzer for determining a diabetic pathological condition of a patient based on the parameter values predicted by the predicting device;
a memory for storing a plurality of diagnostic support data including a treatment policy corresponding to each of a plurality of pathological conditions;
a diagnostic support information generator for generating diagnostic support information including a hypothetical treatment policy corresponding to the diabetic pathological condition by searching the memory;
a treatment simulator that operatively processes the parameter values predicted by the predicting device and a hypothetical treatment from the hypothetical treatment policy received from the diagnostic support information generator and the biological model, respectively, wherein the treatment simulator simulates effects of the treatment of the hypothetical treatment policy; and
a diagnostic support information outputting unit for outputting information obtained by the diagnostic support information generator and information obtained by the treatment simulator.

2. The diagnostic support system for diabetes of claim 1, wherein the biological model comprises model structures common to each of a plurality of patients.

3. The diagnostic support system for diabetes of claim 1, wherein the parameters correspond to a pathological condition related to the treatment of diabetes.

4. The diagnostic support system for diabetes of claim 1, wherein the predicting device predicts the parameter values of a biological model so as to produce agreement between the input diagnostic data and a behavior of a living body recreated in the biological model.

5. The diagnostic support system for diabetes of claim 4, wherein the diagnostic data comprises a patient blood glucose level and an insulin concentration; and wherein the predicting device predicts the parameter values of the biological model so as to conform a blood glucose level and an insulin concentration of the biological model to the patient blood glucose level and insulin concentration.

6. The diagnostic support system for diabetes of claim 1, wherein the pathological condition analyzer determines the pathological condition of the patient by comparing the parameter values characteristic of the patient with a predetermined normal range of the parameter values.

7. The diagnostic support system for diabetes of claim 1, wherein the memory stores a plurality of diagnostic support information items corresponding to each of a plurality of pathological condition patterns;
wherein the pathological condition analyzer determines a pathological condition pattern as the pathological condition; and
wherein the diagnostic support information generator generates diagnostic support information corresponding to the pathological condition pattern by searching the memory.

8. The diagnostic support system for diabetes of claim 1, wherein the hypothetical treatment policy includes a dosage of a medication.

9. The diagnostic support system for diabetes of claim 8, wherein the biological model comprises model structures common to each of the plurality of patients.

10. The diagnostic support system for diabetes of claim 8, wherein the predicting device predicts the parameter values of the biological model so as to produce an agreement between the input diagnostic data and behavior of a living body recreated in the biological model.

11. The diagnostic support system for diabetes of claim 10, wherein the diagnostic data comprises a patient blood glucose level and an insulin concentration; and wherein the predicting device predicts the parameter values of the biological model so as to conform a blood glucose level and an insulin concentration of the biological model to the patient blood glucose level and insulin concentration.

12. The diagnostic support system for diabetes of claim 1, wherein the diagnostic support information includes information of a dosage of a medication corresponding to the diabetic pathological condition.

13. A computer-readable storage medium for recording a computer program which enables a computer provided with an input device and an output device to function as a diagnostic support system for diabetes, wherein the computer program enables the computer to perform predetermined operations comprising:
receiving diagnostic data which includes clinical testing data through the input device;
predicting parameter values through a predictor device which are suited for a patient based on the diagnostic data and a biological model having a predetermined parameter and which represents an organ function related to diabetes as a numerical model,
wherein the biological model includes pancreas, liver, and peripheral tissue models, and the pancreas model represents insulin secretion, the liver model represents glucose uptake and production, and the peripheral tissue model represents glucose metabolism through insulin, and
wherein the biological model comprises parameters which respectively represent non-insulin-dependent glucose metabolism rate, basal glucose level, insulin uptake function at the insulin action site, insulin consumption rate relative to an insulin-dependent glucose metabolism, basal insulin concentration, amount of insulin consumed per unit time, insulin secretion sensitivity relative to glucose stimulation, and blood glucose level threshold at which insulin secretion begins;

determining one or more diabetic pathological conditions of a patient based on the predicted parameter values;

generating diagnostic support information corresponding to a determined diabetic pathological condition by searching a memory that stores a plurality of diagnostic support data corresponding to each of the one or more diabetic pathological conditions;

processing the parameter values predicted by the predictor device and a treatment of a hypothetical treatment policy generated from the diagnostic support information and the biological model, respectively;

simulating effects of the treatment of the hypothetical treatment policy; and outputting the diagnostic support information and the simulated effects of the treatment through the output device.

14. The storage medium of claim 13, wherein the biological model comprises model structures common to each a plurality of patients.

15. The storage medium of claim 13, wherein the predetermined parameter corresponds to a pathological condition related to the treatment of diabetes.

16. The storage medium of claim 13, wherein the predicting of the parameter values comprise predicting the parameter values of the biological model so as to produce agreement between the input diagnostic data and a behavior of a living body recreated in the biological model.

17. A diagnostic support system for diabetes comprising:

an input interface configured to receive diagnostic data comprising clinical testing data of a patient to be input to a computerized predicting device that predicts parameter values suited for the patient based on measured deviations between the diagnostic data and a biological model, wherein the computerized biological model simulates an organ function related to diabetes through a numerical model, wherein the biological model includes pancreas, liver, and peripheral tissue models, and the pancreas model represents insulin secretion, the liver model represents glucose uptake and production, and the peripheral tissue model represents glucose metabolism through insulin, and wherein the biological model comprises parameters which respectively represent non-insulin-dependent glucose metabolism rate, basal glucose level, insulin uptake function at the insulin action site, insulin consumption rate relative to an insulin dependent glucose metabolism, basal insulin concentration, amount of insulin consumed per unit time, insulin secretion sensitivity relative to glucose stimulation, and blood glucose level threshold at which insulin secretion begins;

a pathological condition analyzer that determines one or more diabetic pathological conditions of the patient based on an output of the computerized predicting device;

a memory that retains a plurality of diagnostic support data that comprises a treatment policy corresponding to each of the one or more diabetic pathological conditions;

a diagnostic support information generator that generates diagnostic support information and a hypothetical treatment policy corresponding to the one or more diabetic pathological conditions;

a treatment simulator that operatively processes the parameter values generated by the computerized predicting device that reflects a disease condition after a hypothetical treatment, the treatment simulator simulates effects of the hypothetical treatment and the treatment simulator is operatively coupled to the diagnostic support information generator and the biological model; and a computerized diagnostic support unit that outputs treatment methods generated by the diagnostic support information generator and predicted treatment results from the treatment simulator.

* * * * *